US011198767B2

(12) United States Patent
Guemard et al.

(10) Patent No.: US 11,198,767 B2
(45) Date of Patent: Dec. 14, 2021

(54) PROCESS FOR PREPARING A BIODEGRADABLE PLASTIC COMPOSITION

(71) Applicant: CARBIOS, Saint-Beauzire (FR)

(72) Inventors: Elodie Guemard, Chamalieres (FR); Michel Chateau, Riom (FR); Alain Marty, Toulouse (FR)

(73) Assignee: CARBIOS, Saint-Beauzire (FR)

( * ) Notice: Subject to any disclaimer, the term of this patent is extended or adjusted under 35 U.S.C. 154(b) by 397 days.

(21) Appl. No.: 15/580,735

(22) PCT Filed: Jun. 10, 2016

(86) PCT No.: PCT/EP2016/063373
§ 371 (c)(1),
(2) Date: Dec. 8, 2017

(87) PCT Pub. No.: WO2016/198652
PCT Pub. Date: Dec. 15, 2016

(65) Prior Publication Data
US 2018/0142097 A1 May 24, 2018

(30) Foreign Application Priority Data
Jun. 12, 2015 (EP) .................................... 15305903

(51) Int. Cl.
*C12N 9/20* (2006.01)
*C12N 9/50* (2006.01)
*C12N 9/52* (2006.01)
*C08J 3/22* (2006.01)
*B29C 48/40* (2019.01)
*C08L 101/16* (2006.01)
*C08J 3/20* (2006.01)
*C08L 67/02* (2006.01)
*C08L 3/02* (2006.01)
*C08L 89/00* (2006.01)
*C08L 67/04* (2006.01)
*C08J 5/00* (2006.01)
*C08J 5/18* (2006.01)
*C08K 3/26* (2006.01)
*C08K 3/34* (2006.01)
*C08K 5/00* (2006.01)
*C08K 7/14* (2006.01)
*C08L 99/00* (2006.01)
*C08K 3/22* (2006.01)

(52) U.S. Cl.
CPC ............. *C08J 3/226* (2013.01); *B29C 48/402* (2019.02); *C08J 3/20* (2013.01); *C08J 3/203* (2013.01); *C08J 5/00* (2013.01); *C08J 5/18* (2013.01); *C08K 3/26* (2013.01); *C08K 3/34* (2013.01); *C08K 5/0033* (2013.01); *C08K 7/14* (2013.01); *C08L 3/02* (2013.01); *C08L 67/02* (2013.01); *C08L 67/04* (2013.01); *C08L 89/00* (2013.01); *C08L 99/00* (2013.01); *C08L 101/16* (2013.01); *C12N 9/20* (2013.01); *C12N 9/50* (2013.01); *C12N 9/52* (2013.01); *C12Y 304/21062* (2013.01); *C08J 2300/16* (2013.01); *C08J 2301/02* (2013.01); *C08J 2303/04* (2013.01); *C08J 2323/02* (2013.01); *C08J 2333/24* (2013.01); *C08J 2367/00* (2013.01); *C08J 2367/04* (2013.01); *C08J 2489/00* (2013.01); *C08K 2003/2206* (2013.01); *C08K 2003/265* (2013.01); *C08K 2201/018* (2013.01); *C08L 2201/06* (2013.01)

(58) Field of Classification Search
CPC . C08J 3/226; C08J 3/20; C08J 2301/02; C08J 2303/04; C08J 2323/02; C08J 2333/24; C08J 2300/16; C08J 2367/04; C08J 2489/00; C08J 2367/00; C08J 3/203; C08J 5/00; C08J 5/18; B29C 48/402; C12N 9/20; C12N 9/50; C12N 9/52; C12Y 304/21062; C08K 2003/2206; C08K 2003/265; C08K 2201/018; C08K 3/22; C08K 3/26; C08K 3/34; C08K 5/0033; C08K 7/14; C08L 2201/06; C08L 67/02; C08L 3/02; C08L 89/00; C08L 99/00; C08L 101/16; C08L 67/04
See application file for complete search history.

(56) References Cited

U.S. PATENT DOCUMENTS

| 5,032,512 A | 7/1991 | Witholt et al. |
| 5,145,779 A | 9/1992 | Pometto et al. |
| 5,212,219 A | 5/1993 | Griffin |
| 5,316,847 A | 5/1994 | Suominen |

(Continued)

FOREIGN PATENT DOCUMENTS

| CN | 101 457 218 | 6/2009 |
| CN | 102250379 | 11/2011 |

(Continued)

OTHER PUBLICATIONS

Written Opinion in International Application No. PCT/EP2016/063373, dated Aug. 8, 2017, pp. 1-7.

(Continued)

*Primary Examiner* — Delia M Ramirez
(74) *Attorney, Agent, or Firm* — Saliwanchik, Lloyd & Eisenschenk

(57) ABSTRACT

The present invention relates to plastic composition comprising at least one polyester, biological entities having a polyester-degrading activity and at least an anti-acid filler, wherein the biological entities represent less than 11% by weight, based on the total weight of the plastic composition, and uses thereof for manufacturing biodegradable plastic articles.

9 Claims, 3 Drawing Sheets

(56) References Cited

U.S. PATENT DOCUMENTS

| | | |
|---|---|---|
| 5,378,738 A | 1/1995 | Deguchi et al. |
| 5,426,047 A | 6/1995 | Ito et al. |
| 6,312,578 B1 | 11/2001 | Canivenc et al. |
| 6,429,006 B1 | 8/2002 | Porro et al. |
| 7,465,575 B2 | 12/2008 | Nilsson |
| 7,534,597 B2 | 5/2009 | Hause et al. |
| 7,960,154 B1 | 6/2011 | Nakajima et al. |
| 8,137,953 B2 | 3/2012 | Miller et al. |
| 8,476,056 B2 | 7/2013 | Hoang et al. |
| 8,614,076 B2 | 12/2013 | Wada et al. |
| 8,859,260 B2 | 10/2014 | Sawai et al. |
| 9,476,073 B2 | 10/2016 | Boisart |
| 9,528,132 B2 | 12/2016 | Mazzoli et al. |
| 10,124,512 B2 | 11/2018 | Boisart et al. |
| 2005/0261465 A1 | 11/2005 | Nagarajan |
| 2006/0106120 A1 | 5/2006 | Abe et al. |
| 2008/0242784 A1 | 10/2008 | Ganesan et al. |
| 2011/0008855 A1 | 1/2011 | Park et al. |
| 2011/0200771 A1 | 8/2011 | Barclay |
| 2011/0245057 A1 | 10/2011 | Scoledes et al. |
| 2011/0319588 A1 | 12/2011 | Coupin et al. |
| 2012/0184005 A1 | 7/2012 | Ferreira et al. |
| 2013/0274373 A1 | 10/2013 | Yoshikawa et al. |
| 2014/0303278 A1 | 10/2014 | Ferreira et al. |
| 2015/0056673 A1 | 2/2015 | Boisart |
| 2015/0290840 A1 | 10/2015 | Boisart et al. |
| 2016/0280881 A1 | 9/2016 | Boisart et al. |
| 2017/0114205 A1 | 4/2017 | Maille |
| 2017/0313998 A1 | 11/2017 | Alvarez et al. |
| 2017/0349723 A1 | 12/2017 | Ferreira et al. |
| 2018/0051264 A1 | 2/2018 | Li et al. |
| 2018/0186943 A1 | 7/2018 | Chateau et al. |

FOREIGN PATENT DOCUMENTS

| | | |
|---|---|---|
| CN | 102675712 | 9/2012 |
| CN | 103937179 | 7/2014 |
| CN | 103980535 | 8/2014 |
| EP | 0 421 413 | 4/1991 |
| EP | 0 738 752 | 10/1996 |
| EP | 1 548 053 | 6/2005 |
| EP | 2 013 280 | 1/2009 |
| EP | 2 348 122 | 7/2011 |
| EP | 2 377 945 | 10/2011 |
| EP | 2 471 910 | 7/2012 |
| EP | 2 626 386 | 8/2013 |
| JP | H09-118842 | 5/1997 |
| JP | 2000-506442 | 5/2000 |
| JP | 2002-293982 | 10/2002 |
| JP | 2002-320499 | 11/2002 |
| JP | 2002 362578 | 12/2002 |
| JP | 2003-079388 | 3/2003 |
| JP | 2003-128835 | 5/2003 |
| JP | 2004 058010 | 2/2004 |
| JP | 2004-290130 | 10/2004 |
| JP | 2004 292705 | 10/2004 |
| JP | 2007 319092 | 12/2007 |
| JP | 2012 149273 | 8/2012 |
| JP | 2012-152171 | 8/2012 |
| JP | 2013 000099 | 1/2013 |
| JP | 5 630597 | 11/2014 |
| KR | 20110045975 | 5/2011 |
| WO | WO 89/10381 | 11/1989 |
| WO | WO 2005/026245 | 3/2005 |
| WO | WO 2010/012805 | 2/2010 |
| WO | WO 2010/081887 | 7/2010 |
| WO | WO 2011/039489 | 4/2011 |
| WO | WO 2013/144239 | 10/2013 |
| WO | WO 2014/079844 | 5/2014 |
| WO | WO 2014/122698 | 8/2014 |
| WO | WO 2014/167518 | 10/2014 |
| WO | WO 2014/167562 | 10/2014 |
| WO | WO 2015/067619 | 5/2015 |
| WO | WO 2015/097104 | 7/2015 |
| WO | WO 2015/173265 | 11/2015 |
| WO | WO 2016/198650 | 12/2016 |
| WO | WO 2016/198652 | 12/2016 |
| WO | WO 2017/108577 | 6/2017 |
| WO | WO 2017/198786 | 11/2017 |

OTHER PUBLICATIONS

Written Opinion in International Application No. PCT/EP2017/062028, dated Jun. 30, 2017, pp. 1-5.

Matsuda, E. et al. "Gene Cloning and Molecular Characterization of an Extracellular Poly($_L$-Lactic Acid) Depolymerase from *Amycolatopsis* sp. Strain K104-1" *Journal of Bacteriology*, Nov. 2005, pp. 7333-7340, vol. 187, No. 21.

Database WPI, Accession No. 2009-K99963, Jun. 17, 2009, pp. 1-2, XP-002690934.

Database WPI, Accession No. 2008-F66138, Dec. 13, 2007, pp. 1-2, XP-002690935.

Wang, Z.-Y. et al. "Gene Cloning and Characterization of a Poly($_L$-Lactic Acid) Depolymerase from *Pseudomonas* sp. Strain DS04-T" *J Polym Environ*, Aug. 28, 2011, pp. 827-833, vol. 19, No. 4.

Akutsu-Shigeno, Y. et al. "Cloning and Sequencing of a Poly($_{DL}$-Lactic Acid) Depolymerase Gene from *Paenibacillus amylolyticus* Strain TB-13 and Its Functional Expression in *Escherichia coli*" *Applied and Environmental Microbiology*, May 2003, pp. 2498-2504, vol. 69, No. 5.

Petrov, K et al. "$_L$(+)—Lactic acid production from starch by a novel amylolytic *Lactococcus lactis* subsp. *lactis* 884" *Food Microbiology*, Jun. 2008, pp. 550-557, vol. 25.

Currently pending claims of U.S. Appl. No. 14/443,524, 2016, pp. 1-4.

Bernard, N. et al. "Cloning of the D-lactate dehydrogenase gene from *Lactobacillus delbrueckii* subsp. *bulgaricus* by complementation in *Escherichia coli*" *FEBS*, Sep. 1991, pp. 61-64, No. 1.

Wieczorek, A. et al. "Engineering the cell surface display of cohesins for assembly of cellulosome-inspired enzyme complexes on *Lactococcus lactis*" *Microbial Cell Factories*, Sep. 2010, pp. 1-13, Vo. 9, No. 69.

Wieczorek, A. et al. "Effects of synthetic cohesin-containing scaffold protein architecture on binding dockerin-enzyme fusions on the surface of *Lactococcus lactis*" *Microbial Cell Factories*, 2012, pp. 1-13, vol. 160, No. 11.

Koukiekolo, R. et al. "Degradation of Corn Fiber by *Clostridium cellulovorans* Cellulases and Hemicellulases and Contribution of Scaffolding Protein CbpA" Applied and Environmental Microbiology, Jul. 1, 2005, pp. 3504-3511, vol. 71, No. 7.

Cha, J. et al. "Effect of Multiple Copies of Cohesins on Cellulase and Hemicellulase Activities of *Clostridium cellulovorans* Mini-cellulosomes" *Journal of Microbiology and Biotechnology*, 2007, pp. 1782-1788, vol. 17, No. 11.

Kataeva, I. et al. "Interaction between *Clostridium thermocellum* endoglucanase CelD and polypeptides derived from the cellulosome-integrating protein CipA: stoichiometry and cellulolytic activity of the complexes" *Biochemical Journal*, 1997, pp. 617-624, vol. 326, No. 2.

Wen, F. et al. "Yeast Surface Display of Trifunctional Minicellulosomes for Simultaneous Saccharification and Fermentation of Cellulose to Ethanol" Applied and Environmental Microbiology, Feb. 1, 2010, pp. 1251-1260, vol. 76, No. 4.

Hyeon, J. E. et al. "Production of minicellulosomes for the enhanced hydrolysis of cellulosic substrates by recombinant *Corynebacterium glutamicum*" *Enzyme and Microbial Technology*, 2011, pp. 371-377, vol. 48.

Sun, J. et al. "Direct Conversion of Xylan to Ethanol by Recombinant *Saccharomyces cerevisiae* Strains Displaying an Engineered Minihemicellulosome" Applied and Environmental Microbiology, Jun. 2012, pp. 3837-3845, vol. 78, No. 11.

Database EMBL [Online] Accession No. HC441374, "Sequence 9 from Patent WO2010012805" Feb. 20, 2010, pp. 1-3, XP-002697306.

Database Geneseq [Online] Accession No. AZM34659, "*Clostridium* sp. Cellulose-binding protein-A (CbpA) DNA SEQ: 6" Oct. 13, 2011, p. 1, XP-002697307.

(56) References Cited

OTHER PUBLICATIONS

Written Opinion in International Application No. PCT/EP2013/061413, dated Aug. 5, 2013, pp. 1-7.
Devos, D. et al. "Practical Limits of Function Prediction" *Proteins: Structure, Function and Genetics*, 2000, pp. 98-107, vol. 41.
Whisstock, J. C. et al. "Prediction of protein function from protein sequence and structure" *Quarterly Reviews of Biophysics*, 2003, pp. 307-340, vol. 36, No. 3.
Witkowski, A. et al. "Conversion of a β-Ketoacyl Synthase to a Malonyl Decarboxylase by Replacement of the Active-Site Cysteine with Glutamine" *Biochemistry*, 1999, p. 11643-11650, vol. 38.
Kisselev, L. "Polypeptide Release Factors in Prokaryotes and Eukaryotes: Same Function, Different Structure" *Structure*, Jan. 2002, pp. 8-9, vol. 10.
Database WPI, Accession No. 2005-262580, Mar. 24, 2005, pp. 1-3, XP-002690554.
Database WPI, Accession No. 2004-751104, Oct. 21, 2004, pp. 1-2, XP-002690555.
Currently pending claims of U.S. Appl. No. 14/387,285, 2014, pp. 1-3.
Yoshida, S. et al. "A bacterium that degrades and assimilates poly(ethylene terephthalate)" *Science*, Mar. 11, 2016, pp. 1196-1199, vol. 351.
Demirel, B. et al. "Crystallization Behavior of PET Materials" *BAU Fen Bil. Enst. Dergisi Cilt*, 2011, pp. 26-35, vol. 13, No. 1.
Kyrikou, I. et al. "Biodegradation of Agricultural Plastic Films: A Critical review" *J Polym Environ*, 2007, pp. 125-150, vol. 15.
Chen, S. et al. "Identification and Characterization of Bacterial Cutinase" *The Journal of Biological Chemistry*, Sep. 19, 2008, pp. 25854-25862, vol. 238, No. 38.
Ronkvist, A. M. et al. "Cutinase-Catalyzed Hydrolysis of Poly(ethylene terephthalate)" *Macromolecules*, 2009, pp. 5128-5138, vol. 42.
Nabil, H. et al. "Recycled Polyethylene Terephthalate Filled Natural Rubber Compounds: Effects of Filler Loading and Types of Matrix" *Journal of Elastomers and Plastics*, 2011, pp. 1-21, vol. 00-2011.
Bartolome, L. et al. "Recent Developments in the Chemical Recycling of PET" Material Recycling—Trends and Perspectives, Mar. 16, 2012, pp. 1-21.
Arutchelvi, J. et al. "Biodegradation of polyethylene and polypropylene" *Indian Journal of Biotechnology*, Jan. 2008, pp. 9-22, vol. 7.
Iwamoto, A. et al. "Enzymatic degradation of plastics containing polycaprolactone" *Polymer Degradation and Stability*, Jan. 1, 1994, pp. 205-213, vol. 45.
Mueller, R.-J. "Biological degradation of synthetic polyesters—Enzymes as potential catalysts for polyester recycling" *Process Biochemistry*, 2006, pp. 2124-2128, vol. 41, No. 10.
Written Opinion in International Application No. PCT/EP2014/073742, dated Aug. 8, 2015, pp. 1-5.
Herrero Acero, E. et al. "Enzymatic Surface Hydrolysis of PET: Effect of Structural Diversity on Kinetic Properties of Cutinases from *Thermobifida*" *Macromolecules*, 2011, pp. 4632-4640, vol. 44, No. 12.
Herrero Acero, E. et al. "Surface Engineering of a Cutinase From *Thermobifida Cellulosilytica* for Improved Polyester Hydrolysis" *Biotechnology & Bioengineering*, Oct. 2013, pp. 2581-2590, vol. 110, No. 10.
Shah, A. A. et al. "Degradation of aliphatic and aliphatic-aromatic co-polyesters by depolymerases from *Roseateles depolymerans* strain TB-87 and analysis of degradation products by LC-MS" *Polymer Degradation and Stability*, Oct. 16, 2013, pp. 2722-2729, vol. 98, No. 12.

Written Opinion in International Application No. PCT/EP2015/060521, dated Jul. 20, 2015, pp. 1-6.
Wikipedia, https://web.archive.org/web/20130424032652/https://en.wikipedia.org/wiki/Polyethylene_terephthalate, archived Apr. 24, 2013, accessed Aug. 13, 2018, pp. 1-13.
Sukkhum, S. et al. "A novel poly($_L$-lactide) degrading actinomycetes isolated from Thai forest soil, phylogenic relationship and the enzyme characterization" *The Journal of General and Applied Microbiology*, 2009, pp. 459-467, vol. 55, No. 6.
Sukkhum, S. et al. "Poly($_L$-Lactide)-Degrading Enzyme Production by *Actinomadura keratinilytica* T16-1 in 3 L Airlift Bioreactor and Its Degradation Ability for Biological Recycle" *Journal of Microbiology and Biotechnology*, Jan. 28, 2012, pp. 92-99, vol. 22, No. 1.
Written Opinion in International Application No. PCT/EP2015/074222, dated Feb. 1, 2016, pp. 1-5.
Niaounakis, 2013. Chapter 4: Disposal. Biopolymers Reuse, Recycling, and Disposal. A Volume in Plastics Design Library, a PDL Handbook Series. ISBN 978-1-4557-3145-9, published by Elsevier Inc, pp. 107-150.
Sugimori, Mar. 2013. Protease, washing agent containing the protease, and method of manufacturing the washing agent. EMBL AB809463, pp. 1-2.
Albertsson, A-C. et al. "Chemistry and biochemistry of polymer biodegradation" *Chemistry and Technology of Biodegradable Polymers*, Jan. 1, 1994, pp. 7-17, Section 2.
Database WPI [Online] Accession No. 2012-Q50933, Sep. 9, 2012, p. 1, XP-002740253.
Database WPI [Online] Accession No. 2004-046313, May 8, 2003, pp. 1-2, XP-002740254.
Written Opinion in International Application No. PCT/EP2015/080557, dated Feb. 3, 2016, pp. 1-6.
Gouda, M. K. et al. "Production of a Polyester Degrading Extracellular Hydrolase from *Thermomonospora fusca*" *Biotechnology Progress*, Sep. 2002, pp. 927-934, vol. 18, No. 5.
Oda, Y. et al. "Degradation of Polylactide by Commercial Proteases" *Journal of Polymers and the Environment*, Jan. 2000, pp. 29-32, vol. 8, No. 1.
Written Opinion in International Application No. PCT/EP2016/055348, dated Jun. 2, 2016, pp. 1-6.
Database UniProt [Online] Accession No. I0LED3, Jun. 13, 2012, pp. 1-2, XP-002743807.
Database Geneseq [Online] Accession No. BAJ28992, Jan. 31, 2013, pp. 1-10, XP-002743803.
Database Geneseq [Online] Accession No. BAJ28991, Jan. 31, 2013, pp. 1-2, XP-002743804.
Database UniProt [Online] Accession No. F4F956, Jun. 28, 2011, pp. 1-2, XP-002743805.
Database UniProt [Online] Accession No. A8LWF7, Dec. 4, 2007, p. 1-2, XP-002743806.
Written Opinion in International Application No. PCT/EP2016/063369, dated Aug. 1, 2016, pp. 1-6.
Okino, S. et al. "Production of D-lactic acid by *Corynebacterium glutamicum* under oxygen deprivation" *Applied Microbiology and Biotechnology*, Jan. 10, 2008, pp. 449-454, vol. 78, No. 3.
Database WPI [Online] Accession No. 2012-K88398, Jan. 27, 2011, pp. 1-2, XP-002759107.
Written Opinion in International Application No. PCT/EP2016/081205, dated Jun. 1, 2017, pp. 1-19.
Currently pending claims of U.S. Appl. No. 16/302,107, 2018, pp. 1-4.
Currently pending claims of U.S. Appl. No. 16/064,494, 2018, pp. 1-3.
Chouzouri, G. et al. "Degradation of Aliphatic Polyesters in the Presence of Inorganic Fillers" *Journal of Plastic Film and Sheeting*, SAGE Publications, 2007, pp. 19-36, vol. 23, No. 1.

PROCESS FOR PREPARING A BIODEGRADABLE PLASTIC COMPOSITION

CROSS-REFERENCE TO RELATED APPLICATION

This application is the U.S. national stage application of International Patent Application No. PCT/EP2016/063373, filed June 10, 2016.

The present invention relates to a novel plastic composition comprising at least one polyester, biological entities able to degrade said polyester and anti-acid filler. The invention also relates to a process for producing such plastic composition, and uses thereof for the production of biodegradable plastic articles.

BACKGROUND

Plastics are inexpensive and durable materials, which are employed to manufacture products that find uses in a wide range of applications. As a consequence, the production of plastics has increased dramatically over the last decades. A large part of these plastics are used for single-use disposable applications, or for short-lived products (such as bags, packaging including trays, containers, bottles, agricultural films, etc.) that are discarded within a year of manufacture. Because of the durability of the polymers involved and their high resistance to biodegradation (due to high molecular mass values, hydrophobicity and crystallinity), substantial quantities of plastics are piling up in landfill sites and in natural habitats, generating increasing environmental problems worldwide.

To answer these problems, different physical, chemical and/or biochemical approaches have been developed to reduce the biodegradation resistance of polymers and to increase their biodegradation rate. For example, biodegradable plastic products have been developed. However, the environmental degradation conditions are not optimal for such biodegradable plastics and their degradation generally takes place partially.

Recently, a novel plastic material has been developed that contains a small amount of biological entities having a polymer-degrading activity. The biological entities are interestingly able to degrade at least one polymer of said plastic material. The process for manufacturing such plastic material has been described in patent application WO 2013/093355. The plastic material obtained by this process contains biological entities dispersed in a polymer, and is directly usable through an extrusion die for producing plastic articles having improved biodegradability.

By working on polyester-containing plastic material, the inventors have discovered that it is possible to further increase the polyester-degrading activity of biological entities, by introducing into the plastic material specific filler(s). More particularly, the inventors have developed plastic compositions containing at least one polyester, biological entities having a polyester-degrading activity and anti-acid filler(s), and they have shown that such compositions have an improved biodegradability compared to traditional plastic compositions, and even compared to plastic compositions containing solely biological entities and polyesters. Furthermore, the plastic compositions of the invention can be used in standard operations of plastic processing and do not impair the mechanical properties of the resulting plastic articles.

SUMMARY OF THE INVENTION

The present invention relates to the use of anti-acid filler(s) to enhance the polyester degrading activity of biological entities into a plastic composition. More particularly, the invention proposes to add both anti-acid filler(s) and biological entities having a polyester degrading activity into a polyester-containing plastic composition to obtain a plastic composition with biodegradable properties and thereby degradable plastic articles, made from this plastic composition. According to the invention, the biological entities and anti-acid filler(s) are both embedded into the polyester of the plastic composition, leading to a homogenous dispersion of them into the final plastic articles.

It is therefore an object of the present invention to provide a plastic composition comprising at least one polyester, biological entities having a polyester-degrading activity and at least an anti-acid filler, wherein the biological entities represent less than 11% by weight, based on the total weight of the plastic composition.

It is another object of the present invention to provide a plastic composition comprising at least one polyester, biological entities having a polyester-degrading activity and at least an anti-acid filler, wherein the total amount of polymer(s) and anti-acid filler(s) in the plastic composition represent more than 90% by weight of the plastic composition. Advantageously, the anti-acid filler represents between 0.1% and 50% by weight of the plastic composition, based on the total weight of the plastic composition, preferably between 2% and 25%, more preferably between 5% and 10%, even more preferably about 5%.

In a particular embodiment, the plastic composition comprises, based on the total weigh of the plastic composition:
(i) from 65 to 95% of at least one polyester, preferably PLA and/or PCL;
(ii) from 2 to 25% of at least one anti-acid filler, preferably selected from hydrotalcite, calcium carbonate, talc, mica, clay and/or calcium hydroxide;
(iii) from 0.1-10% of biological entities having a polyester-degrading activity, preferably a protease.

It is a further object of the invention to provide a process for preparing such plastic composition, comprising a step (a) of mixing between 0.1% and 10% by weight based on the total weight of the plastic composition of biological entities having a polyester-degrading activity, with a polyester and anti-acid filler(s), and a step (b) of conditioning said mixture of step (a) in a solid form, wherein the step (a) of mixing is preferably performed at a temperature at which the polyester is in a partially or totally molten state and/or in an extruder, preferably a twin-screw extruder, and more preferably a co-rotative twin-screw extruder.

The invention further relates to the use of the plastic composition of the invention, for the manufacture of a plastic article, and to a plastic article made from a plastic composition of the invention, wherein the biological entities of the plastic composition are suitable for degrading at least one polyester of the plastic article.

The invention also relates to a method for manufacturing a plastic article comprising at least one polyester, the method comprising:
a. providing a plastic composition according to the invention, and
b. manufacturing a plastic article,
wherein step b is preferably implemented at a temperature at which the polyester of the plastic composition is in a partially or totally molten state, and/or is performed by extrusion, extrusion-compounding, extrusion blow-molding, blown film extrusion, cast film extrusion, calendering and thermoforming, injection-molding, compression molding, extrusion-swelling, rotary molding, ironing, coating, stratification, expansion, pultrusion, compression-granulation and 3D printing.

In it another object of the invention to provide a method for increasing the biodegradability of a plastic article comprising at least one polyester, said method comprising mixing the polyester with biological entities suitable for degrading said polyester, and with an anti-acid filler to obtained a plastic composition, and further manufacturing a plastic article with said plastic composition.

DETAILED DESCRIPTION OF THE INVENTION

Figure 1:
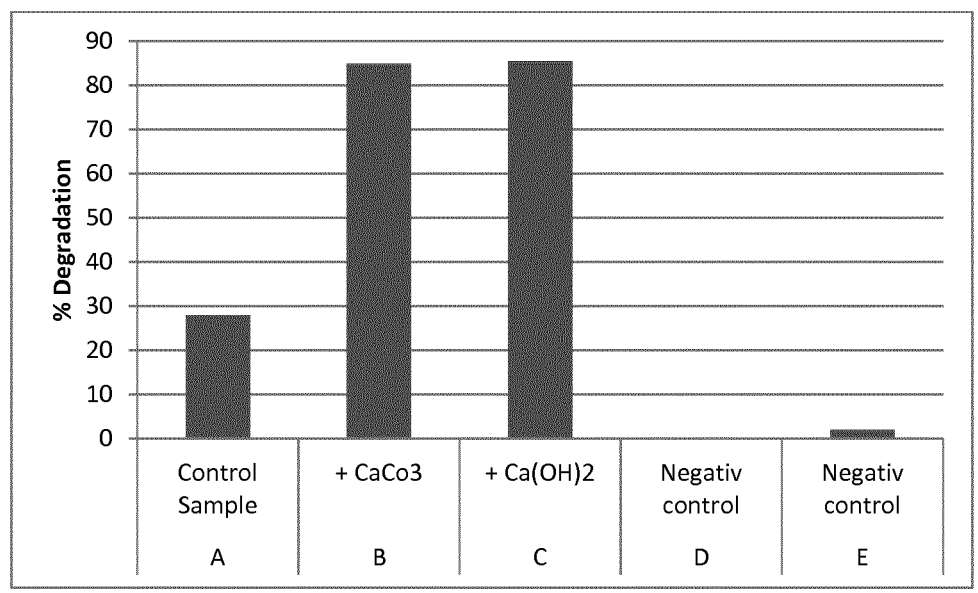
FIG. 1: Comparative degradation rate of plastic compositions containing PLA after 12 days. A: Control (comprising protease but deprived of anti-acid filler) reached 28% of degradation; D and E: Negative controls (comprising anti-acid filler but deprived of protease) reached less than 2% of degradation; B and C: plastic compositions according to the invention (comprising both protease and an anti-acid filler) reached both 85% of degradation.

The present invention relates to novel plastic compositions, with improved degradability and methods for producing them. More particularly, the invention provides novel plastic compositions comprising both biological entities and anti-acid filler suitable for enhancing the degrading activity of said biological entities. The invention shows that such compositions, with suitable dispersion and distribution rate of active biological entities, are particularly useful for producing single-use and short-lived plastic articles.

Definitions

The present disclosure will be best understood by reference to the following definitions.

As used herein, the terms "plastic composition", "plastic formulation", "plastic compound" or "plastic material" are used interchangeably and designate a mixture of polymers and additional compounds (e.g., active agents, additives, carrier material, filler, etc.) before any shaping or conditioning step.

In the context of the invention, a "polyester-containing plastic composition" refers to a plastic compound, or plastic formulation, in a molten or solid state, suitable for making a plastic product. In the context of the invention, the plastic compound encompasses homogeneous blends of at least one polyester, biological entities able to degrade at least said polyester, and at least one anti-acid filler. Preferably, the plastic compound is constituted of a mix of semi-crystalline and/or amorphous polyesters, or semi-crystalline polyesters and additives.

Within the context of the invention, the terms "plastic article" or "plastic product" are used interchangeably and refer to any item made from at least one polymer, such as plastic sheet, tube, rod, profile, shape, massive block, fiber, etc. Preferably, the plastic article is a manufactured product, such as a rigid or flexible packaging, agricultural films, bags and sacks, disposable items or the like. Preferably, the plastic article comprises a mix of semi-crystalline and/or amorphous polymers, or semi-crystalline polymers and additives. The plastic articles may contain additional substances or additives, such as plasticizers, mineral or organic fillers.

A "polymer" refers to a chemical compound or mixture of compounds whose structure is constituted of multiple repeating units linked by covalent chemical bonds. Within the context of the invention, the term "polymer" includes natural or synthetic polymers, comprising a single type of repeating unit (i.e., homopolymers) or different types of repeating units (i.e., block copolymers and random copolymers). As an example, synthetic polymers include polymers derived from petroleum oil or biobased polymers, such as polyolefins, aliphatic or aromatic polyesters, polyamides, polyurethanes and polyvinyl chloride. Natural polymers include lignin and polysaccharides, such as cellulose, hemicellulose, starch and derivatives thereof that may or may not be plasticized.

Within the context of the invention, the term "polyester" refers to a polymer that contains the ester functional group in their main chain. Ester functional group is characterized by a carbon bound to three other atoms: a single bond to a carbon, a double bond to an oxygen, and a single bond to an oxygen. The singly bound oxygen is bound to another carbon. According to the composition of their main chain, polyesters can be aliphatic, aromatic or semi-aromatic. Polyester can be homopolymer or copolymer. As an example, polylactic acid is an aliphatic homopolymer composed of one monomer, lactic acid; and polyethylene terephthalate is an aliphatic-aromatic copolymer composed of two monomers, terephthalic acid and ethylene glycol.

In the context of the invention, the term "filler" refers to a compound that is incorporated to a plastic material and/or to a plastic product to reduce the costs thereof or, optionally, improve the physical properties thereof (e.g., its hardness, stiffness, or strength). Fillers can be inactive (i.e., inert) or active material, and may form chemical bonds with the components of the plastic material or product. Fillers may comprise mineral and/or organic fillers. Examples of mineral fillers used in the plastic manufacturing industry include without limitation calcium carbonate (limestone), magnesium silicates (talc), calcium sulfate (gypsum), mica, calcium silicate, barium sulphate and kaolin (China clay). Examples of organic fillers include without limitation starch, cellulose or hemi-cellulose, cereal flour, wood flour, tree bark flour, nut flours, hemp fibers, chicken feathers, and rice hulls.

In the context of the invention, the term "anti-acid filler" or "acid scavenger" are used interchangeably and designate more specifically a filler that has the ability to chemically neutralize an acid molecule, even contained in a plastic composition. The neutralizing reaction performed by an anti-acid filler, in the context of the invention, is generally based on ion-exchange. The presence of an anti-acid filler in a plastic composition may help to increase and/or maintain the pH of the composition. Anti-acid fillers may be mineral or organic, synthetic or natural, and used alone or as a mix of several anti-acid fillers.

As used herein, the term "biological entities" designates active enzymes or enzyme-producing microorganisms, such as sporulating microorganisms, as well as combinations or formulations thereof. For instance, "biological entities" may refer to pure enzymes or microorganisms as well as to formulations containing enzymes and/or microorganisms and a diluent or carrier, such as stabilizing and/or solubilizing component(s), including water, glycerol, sorbitol, dextrin, including maltodextrin and/or cyclodextrin starch, glycol such as propanediol, salt, etc. The biological entities may be in solid (e.g., powder) or liquid form.

As used herein, the term "by weight" refers to the ratio based on the total weight of the considered composition or product.

In the context of the invention, the term "about" refers to a margin of +/−5%, preferably of +/−1%, or within the tolerance of a suitable measuring device or instrument.

In the context of the invention, all percentages are by weight, based on the total weight of the plastic composition, unless explicitly stated otherwise.

Anti-Acid Filler

The inventors have shown that it is possible to improve the degradability of a plastic composition comprising polyester and biological entities having a polyester-degrading activity by the addition of anti-acid filler. The presence of the anti-acid filler, embedded into the mass of the polyester with the biological entities enhances the activity of said biological entities. More particularly, the depolymerase activity of the biological entities in the polyester-containing plastic composition in presence of anti-acid filler is higher than without such anti-acid filler in the composition. Thereby, the degradation rate of a composition of the invention and/or plastic article made with such composition is improved (i.e., higher) than the degradation rate of composition/plastic article deprived of such anti-acid filler.

It is therefore an object of the invention to provide a plastic composition comprising at least one polyester, biological entities having a polyester-degrading activity and at least an anti-acid filler. According to the invention, such biological entities represent less than 11% by weight of the plastic composition. Particularly, the biological entities represent between 0.1% and 10% by weight of the plastic composition.

It is another object of the invention to provide a method for enhancing the degradability of a polyester-containing plastic composition, or any plastic product made with said plastic composition, wherein both biological entities having polyester-degrading activity and anti-acid filler(s) are added in the plastic composition. Advantageously, both biological entities and anti-acid filler are mixed with the polyester to form the plastic composition that may be further used for manufacturing any plastic products.

The invention further relates to the use of anti-acid filler for enhancing the activity of biological entities, and more particularly their polyester-degrading activity, into a polyester-containing plastic composition.

In a particular embodiment, the plastic composition comprises less than 50%, preferably less than 40%, 30%, 25%, 20%, 10%, 9%, 8%, 7%, 6% by weight of anti-acid filler. Particularly, the plastic composition comprises between 0.1% and 50% by weight of anti-acid filler, preferably between 2% and 25%, more preferably between 2% and 15%, even more preferably between 5% and 10%. In a particular embodiment, the plastic composition comprises about 10% by weight of anti-acid filler. In another embodiment, the plastic composition comprises about 5% by weight of anti-acid filler.

Anti-acid fillers may be mineral or organic. In a particular embodiment, the anti-acid filler is selected among mineral anti-acid fillers. Such mineral anti-acid filler can be synthetic or natural. Examples of mineral anti-acid filler include, without limitation:

- carbonate salts or metal carbonate such as calcium carbonate (or limestone), potassium carbonate, magnesium carbonate, aluminium carbonate, zinc carbonate, copper carbonate
- hydroxide salt or metal hydroxide such as calcium hydroxide or potassium hydroxide (potash) or magnesium hydroxide or aluminium hydroxide or sodium hydroxide (caustic soda)
- silicate salts such as calcium silicate, potassium silicate, magnesium silicates (talc), aluminium silicate (kaolin), or mix thereof such as mica
- hydrotalcite (magnesium aluminum hydroxide carbonate, $Mg_6Al_2CO_3(OH)_{16} \cdot 4(H_2O)$) such as synthetic commercial DHT-4A2 or DHT-4A
- metal oxide or oxide salts such as oxide of magnesium, oxide of calcium, oxide of aluminium, iron oxide, copper oxide
- sulphate salts such as calcium sulfate (gypsum), barium sulphate
- phosphate salts as calcium phosphate, hydroxyapatite
- Clays such vermiculite, palygorskite-sepiolite and clays from smectite such as montmorillonite.

Preferably, the mineral anti-acid filler is selected from calcium carbonate, calcium hydroxide, hydrotalcite, talc, mica, or clay.

It is a particular object of the invention to provide a plastic composition comprising PLA and/or PCL, biological entities able to degrade PLA and/or PCL and between 1 and 50% by weight of calcium carbonate and/or hydrotalcite and/or calcium hydroxide. Preferably, the biological entities comprise a protease selected from Savinase®, Everlase®, Protease enzyme from *Actinomadura keratinilytica* or from *Laceyella sacchari* LP175, lipase PS from *Pseudomonas cepacia*, lipase AK from *Pseudomonas fluorescens*, lipase B from *Candida antarctica* (CalB).

In a particular embodiment, the molar ratio (anti-acid filler)/(acid contained in the polyester) is less than 0.5, preferably less than 0.45, more preferably less than 0.4. For instance, in a PLA-containing plastic composition of the invention, the molar ratio (anti-acid filler)/(lactic acid) is less than 0.5, preferably less than 0.45, more preferably less than 0.4.

Biological Entities

According to the invention, the plastic composition comprises biological entities suitable for degrading at least one polyester contained in said plastic composition. The inventors have shown that the presence of anti-acid filler(s) embedded into a plastic composition with biological entities allows to increase their enzymatic activity and thereby to enhance the degradability of the plastic composition.

In a preferred embodiment, the biological entities comprise at least an enzyme with polyester-degrading activity and/or at least a microorganism expressing, and optionally excreting, an enzyme having a polyester-degrading activity. In a preferred embodiment, the biological entities consist in at least an enzyme with polyester-degrading activity. Examples of suitable enzymes having a polyester-degrading activity for use in the invention include, without limitation, depolymerase, esterase, lipase, cutinase, carboxylesterase, protease, or polyesterase. The enzymes may be in pure or enriched form, or in mixture with other excipients or diluents. A combination of enzymes may be used as well.

In an alternative embodiment, the biological entities comprise microorganisms that produce such enzymes, either naturally or as a result of particular engineering (e.g., recombinant microorganisms). Preferred examples of suitable microorganisms include, without limitation, bacteria, fungi and yeasts. In an embodiment, the biological entities comprise sporulating microorganisms and/or spores thereof.

In a particular embodiment, the biological entities comprise enzymes encapsulated in nanocapsules, enzymes encapsulated in cage molecules, and enzymes aggregated together.

The term "cage molecule" designates a molecule that can be inserted into the structure of said enzymes to stabilize them and to make them resistant to high temperatures. Encapsulation techniques are well known to those skilled in the art and include, for instance, nanoemulsions.

The biological entities may be supplied in a liquid or solid form. For instance, the biological entities may be in a powder form. To this aim, the biological entities may be dried or dehydrated. Methods for drying or dehydrating biological entities such as microorganisms or enzymes are well known to the one skilled in the art and include, without limitation, lyophilisation, freeze-drying, spray-drying, supercritical drying, down-draught evaporation, thin-layer evaporation, centrifugal evaporation, conveyer drying, fluidized bed drying, drum drying or any combination thereof.

In a particular embodiment, the biological entities used to prepare the plastic composition are a formulation of enzymes and/or microorganisms mixed with a diluent or carrier, such as stabilizing and/or solubilizing component(s). For instance, the formulation may be a solution comprising enzymes and/or microorganisms in suspension in water, and optionally additional components, such as glycerol, sorbitol, dextrin, starch, glycol such as propanediol, salt, etc. Alternatively, the formulation may be a powder comprising enzymes and/or microorganisms in powder form mixed with a stabilizing powder, such as maltodextrin.

In a particular embodiment, the biological entities used to prepare the plastic composition are contained in a masterbatch comprising such biological entities mixed with a polymer. Such masterbatch composition may comprise from 11% to 90% by weight of biological entities having a polyester-degrading activity, based on the total weight of the masterbatch composition. Preferably, the polymer of the masterbatch is compatible with the polyester of the plastic composition. Particularly, such polymer is the polyester of the intended plastic composition. The masterbatch is mixed with the polyester of the plastic composition so that the plastic composition comprises between 0.1 and 10% by weight of biological entities.

In another particular embodiment, the biological entities comprise the culture supernatant of a polyester-degrading microorganism. In this regard, a particular object of the invention relates to a plastic composition as defined above, which comprises between 0.1% and 10%, by weight of a culture supernatant of a polymer-degrading microorganism. The supernatant may have been preliminary treated (e.g., mechanically or physically or chemically) to increase the concentration of enzymes and/or to remove other components such as DNA or cell debris.

Plastic Compositions

It is an object of the invention to provide plastic compositions comprising active biological entities embedded with an anti-acid filler in a polyester. The plastic compositions of the invention may be easily used for further preparing plastic articles with improved degradability in environmental conditions.

The plastic composition may be in solid form (e.g., powder or granulates) or in liquid form. Preferably, the plastic composition is in a solid physical form with a melt flow index comprised between 1 to 60 g/10 min. Such melt flow index may be measured by techniques known by a person skilled in the art such as flow extrusion plastometer, or capillary rheometers. The form of the plastic composition may be advantageously adapted to the final purpose of said composition (e.g., the nature of the polymer, the kind of plastic product to be produced, etc.).

Advantageously, the plastic composition comprises at least one polyester selected from polylactic acid (PLA) (such as poly(L-lactic acid) (PLLA), poly(D-lactic acid) (PDLA), poly(D,L-lactic acid) (PDLLA) or PLA stereocomplex (scPLA)), polyglycolic acid (PGA), polyhydroxyalkanoate (PHA), polycaprolactone (PCL), polybutylene succinate (PBS), polybutylene terephthalate (PBT), polyethylene isosorbide terephthalate (PEIT), polybutylene succinate adipate (PBSA), polybutylene adipate terephthalate (PBAT), polyethylene terephthalate (PET), polytrimethylene terephthalate (PTT), polyethylene furanoate (PEF), poly(ethylene adipate) (PEA), polyethylene naphthalate (PEN), and derivatives or blends/mixtures thereof.

In a preferred embodiment, the plastic composition comprises at least PLA and/or PCL, and optionally one or more polyesters preferably selected from PBAT, PBS, PBSA and PHA.

In a particular embodiment, the plastic composition may further comprise at least one natural polymer, preferably selected from cellulose, hemi-cellulose, starch and derivatives. Preferably, the plastic composition of the invention comprises PLA and/or PCL and at least one additional polymer selected from PBAT, starch or flour or mixtures thereof.

In another particular embodiment, the plastic composition comprises PLA and/or PCL and at least one polyolefin.

According to the invention, the plastic composition may further comprise one or more additives. Generally speaking, the additives are used in order to enhance specific properties in the final product (i.e., the final plastic article made with said plastic composition). For instance, the additives may be selected from the group consisting without limitation of plasticizers, coloring agents, processing aids, rheological agents, anti-static agents, anti-UV agents, toughening agents, anti-fogging agents, compatibilizers, slip agents, flame retardant agents, anti-oxidants, light stabilizers, oxygen scavengers, inks, adhesives, fertilizers, and phytosanitary products. Advantageously, the plastic composition comprises less than 25%, by weight of such additives, preferably less than 20%, more preferably less than 10%, even more preferably less than 5%, typically between 0.1 and 4% by weight of such additives.

Alternatively or in addition, the plastic composition may further comprise one or more additional fillers. For instance, such fillers may be selected from the group consisting without limitation of silica, graphite, carbon black, metal fibers or metal flakes, glass fibers, magnetic fillers, aramid fibers, ceramic fibers, saw dust, plant fibers such as flax fibers, wood fibers, hemp fibers, bamboo fibers, chicken feathers and derivatives thereof or blends/mixtures of these materials.

In a particular embodiment, the plastic composition comprises, based on the total weight of the plastic composition:
from 65 to 95% by weight of at least one polyester;
from 2 to 25% by weight of at least one anti-acid filler;
from 0.1 to 10% by weight of biological entities having a polyester-degrading activity; and optionally
at least one additional polymer and/or additive and/or additional filler.

Particularly, the plastic composition comprises, based on the total weight of the plastic composition:
from 65 to 95% by weight of PLA;
from 2 to 25% by weight of at least one anti-acid filler, preferably selected from hydrotalcite, calcium carbonate, calcium hydroxide, talc, mica and clay;
from 0.1 to 10% by weight of protease having a PLA-degrading activity; and optionally
at least one additional polymer and/or one additive and/or one additional filler.

In another particular embodiment, the plastic composition comprises, based on the total weight of the plastic composition:
from 5 to 65% by weight of a first polyester;
from 10 to 60% by weight of a second polyester and/or natural polymer such as starch or flour;
from 2 to 25% by weight of at least one anti-acid filler;
from 0.1 to 10% by weight of biological entities having a degrading activity for the first polyester; and optionally
at least one additive and/or one additional filler.

Particularly, the plastic composition comprises, based on the total weight of the plastic composition:
from 5 to 65% by weight of PLA;
from 10 to 60% by weight of at least an additional polyester selected from PBAT, PHAs, PBS, or PBSA and/or a natural polymer selected from starch or flour;
from 2 to 25% by weight of at least one anti-acid filler selected from hydrotalcite, calcium carbonate, calcium hydroxide, talc, mica and clay;
from 0.1 to 10% by weight of protease having a PLA-degrading activity; and optionally
at least one additive and/or one additional filler.

Table 1 below lists examples of particular plastic compositions according to the invention wherein the anti-acid filler is or comprises $CaCO_3$. Preferably, the polyester is PLA, the biological entities comprise protease having a PLA-degrading activity.

TABLE 1

Composition of biodegradable plastic compositions comprising $CaCO_3$

| Amount of Polyester | Amount of Biological entities | Amount $CaCO_3$. | Amount of additional polymer(s) and/or additional filler(s) and/or additive(s) |
|---|---|---|---|
| 3% to 97% | 0.1 to 10% | 2% | 0% to 94% |
| 8% to 94% | 0.1 to 10% | 5% | 0% to 86% |
| 15% to 89% | 0.1 to 10% | 10% | 0% to 74% |
| 22% to 84% | 0.1 to 10% | 15% | 0% to 62% |
| 29% to 79% | 0.1 to 10% | 20% | 0% to 50% |
| 36% to 74% | 0.1 to 10% | 25% | 0% to 38% |
| 44% to 69% | 0.1 to 10% | 30% | 0% to 25% |
| 58% to 60% | 0.1 to 10% | 40% | 0% to 2% |
| 5% | 0.1 to 10% | 0.1 to 3% | 82% to 94% |
| 10% | 0.1 to 10% | 0.1 to 6% | 74% to 89% |
| 20% | 0.1 to 10% | 0.1 to 13% | 57% to 79% |
| 30% | 0.1 to 10% | 0.1 to 20% | 40% to 69% |
| 40% | 0.1 to 10% | 0.1 to 27% | 23% to 59% |
| 50% | 0.1 to 10% | 0.1 to 34% | 6% to 49% |
| 60% | 0.1 to 10% | 0.1 to 40% | 0% to 39% |
| 70% | 0.1 to 10% | 0.1 to 30% | 0% to 29% |
| 80% | 0.1 to 10% | 0.1 to 20% | 0% to 19% |
| 90% | 0.1 to 10% | 0.1 to 10% | 0% to 9% |

Table 2 below lists examples of particular plastic compositions according to the invention wherein the anti-acid filler is or comprises $CaOH_2$. Such plastic compositions may also contain one or more additive(s) and/or additional filler(s). Preferably, the Polyester is PLA, the biological entities comprise protease having a PLA-degrading activity.

TABLE 2

Composition of biodegradable plastic compositions

| Amount of Polyester | Amount of Biological entities | Amount of $CaOH_2$. | Amount of additional polymer(s) and/or additional filler(s) and/or additive(s) |
|---|---|---|---|
| 4% to 97% | 0.1 to 10% | 2% | 0% to 93% |
| 10% to 94% | 0.1 to 10% | 5% | 0% to 84% |
| 20% to 89% | 0.1 to 10% | 10% | 0% to 69% |
| 30% to 84% | 0.1 to 10% | 15% | 0% to 54% |
| 39% to 79% | 0.1 to 10% | 20% | 0% to 40% |
| 49% to 74% | 0.1 to 10% | 25% | 0% to 25% |
| 59% to 69% | 0.1 to 10% | 30% | 0% to 10% |
| 64% to 66% | 0.1 to 10% | 33% | 0% to 2% |
| 5% | 0.1 to 10% | 0.1 to 2% | 83% to 94% |
| 10% | 0.1 to 10% | 0.1 to 5% | 75% to 89% |
| 20% | 0.1 to 10% | 0.1 to 10% | 60% to 79% |
| 30% | 0.1 to 10% | 0.1 to 15% | 45% to 69% |
| 40% | 0.1 to 10% | 0.1 to 20% | 30% to 59% |
| 50% | 0.1 to 10% | 0.1 to 25% | 15% to 49% |
| 60% | 0.1 to 10% | 0.1 to 30% | 0% to 39% |
| 70% | 0.1 to 10% | 0.1 to 30% | 0% to 29% |
| 80% | 0.1 to 10% | 0.1 to 20% | 0% to 19% |
| 90% | 0.1 to 10% | 0.1 to 10% | 0% to 9% |

In a particular embodiment, the plastic composition is a biodegradable plastic composition complying with at least one of the relevant standards and/or labels known by a person skilled in the art such as standard EN 13432, standard ASTM D6400, OK Biodegradation Soil (Label Vincotte), OK Biodegradation Water (Label Vincotte), OK Compost (Label Vincotte), OK Compost Home (Label Vincotte).

A biodegradable plastic composition refers to a plastic composition that is at least partially transformed under environmental conditions into oligomers and/or monomers of at least one polyester of the plastic composition, water, carbon dioxide or methane and biomass. As illustrated in the examples, preferred plastic compositions of the invention are biodegradable in water. Preferably, about 90% by weight of the plastic composition is biodegraded in water within less than 90 days, more preferably within less than 60 days, even more preferably within less than 30 days. Alternatively or in addition, the plastic composition may be biodegraded when exposed to wet and temperature conditions that occur in landscape. Preferably, about 90% by weight of the plastic composition is biodegraded with less than 3 years in the environment, more preferably within less than 2 years, even more preferably within less than 1 year. Alternatively, the plastic composition may be biodegraded under industrial composting conditions, wherein the temperature is maintained above 50° C.

Process for Producing the Plastic Compositions

The present invention also relates to a process for preparing a plastic composition as described above, comprising a step (a) of mixing 0.1% to 10% by weight of biological entities having a polyester-degrading activity, with a polyester and an anti-acid filler, and, optionally, a step (b) of conditioning said mixture of step (a) in a solid form. In a particular embodiment, the process further comprises a step of mixing at least one additive with the polyester, biological entities and anti-acid filler, before step (b). Alternatively, such additive can be mixed in step (a) with the polyester, biological entities and anti-acid filler.

In a particular embodiment, step (a) of mixing is performed at ambient temperature, i.e., a temperature below 45° C., preferably below 35° C., more preferably between 30° C. and 20° C., by mixing powders and/or liquids.

In a particular embodiment, the polyester used in step (a) is under a granulated form. In another embodiment, the polyester, the anti-acid filler and the biological entities are under powder form. To this aim, the polyester and/or the anti-acid filler and/or the biological entities can be mechanically pre-treated before step (a) of mixing, to lead to such powder forms. Particularly, the polyester and/or the anti-acid filler may be crushed, and/or the biological entities may be dried or dehydrated. Preferably, the process further comprises a step of homogenisation of the powders (i.e., polyester and anti-acid filler and biological entities), for instance by shaking or the like. Such powder mixture may be blended into an extruder, such as single-screw extruders, multi-screw extruders of either co-rotating or counter-rotating design, dispersive kneaders, reciprocating single-screw extruder (co-kneaders). Such extrusion step may ensure uniformity and homogeneity of the dispersion of both biological entities and anti-acid filler in the polyester-containing composition.

Alternatively, step (a) of mixing is performed with liquid forms of polyester, anti-acid filler and/or biological entities. For instance, the polyester and/or the anti-acid filler are diluted in a liquid before step (a) and/or a liquid formulation of biological entities that may comprise stabilizing and/or solubilizing component(s) is used.

Alternatively, step (a) of mixing is performed at a temperature at which the polyester is in a partially or totally molten state. The step (a) of mixing may thus be performed at a temperature at or above 40° C., particularly at or above 45° C., 55° C., 60° C., 70° C., 80° C., 90° C., 100° C., or even above 150° C., depending on the nature of the polyester. Typically, this temperature does not exceed 300° C. More particularly, the temperature does not exceed 250° C. The temperature of the mixing step can be adapted by a person skilled in the art depending on the type of polyester, biological entities, and/or anti-acid filler used for the production of the plastic composition. Particularly, the temperature is chosen according to the melting point, or melting temperature of the polyester. In a particular embodiment, step (a) of mixing is performed at the melting point of the polyester of the plastic composition. The polyester is then in a partially or totally molten state. In another embodiment, step (a) of mixing is performed at a temperature above the glass transition temperature of said polyester, particularly between the glass transition temperature (Tg) and the melting temperature of said polyester. In another particular embodiment, the step (a) of mixing is performed at a temperature above the melting temperature of said polyester.

In a particular embodiment, the plastic composition may be produced by a process called "compounding", usually an extrusion-granulation process, in which the polyester is melted and mixed with the biological entities and the anti-acid filler. Compounding combines mixing and blending techniques during a heat process, in order to ensure uniformity, homogeneity and dispersion in the final compound. The compounding is a technique known by a person skilled in the art. Such compounding process may be carried out with an extruder, such as single-screw extruders, multi-screw extruders of either co-rotating or counter-rotating design, dispersive kneaders, reciprocating single-screw extruder (co-kneaders).

More generally, the step (a) of mixing may be carried out with an extruder, wherein the polyester is heated and melted and mixed with the biological entities and the anti-acid filler. The polyester may be introduced in the extruder in a powder or granulated form, preferably in a granulated form.

In a preferred embodiment, the extruder used for the production of the plastic composition is a multi-screw extruder, preferably a twin-screw extruder, more preferably a co-rotative twin-screw extruder. In a particular embodiment, the extruder further comprises, after the screws, a static mixer. In another embodiment, the extruder is used with a die pierced with hole(s).

In a preferred embodiment, the residence time of the mixture in the extruder is comprised between 5 seconds and 3 minutes, preferably is less than 2 minutes, more preferably less than 1 minute. When the plastic composition comprises a polyester with a melting temperature below 150° C., the residence time of the mixture in the extruder is preferably less than 2 minutes.

One skilled in the art will easily adapt the characteristics of the extruder (e.g., the length and diameter of the screw(s), etc.), and the residence time to the polyester, the biological entities, and the type of plastic composition intended.

As disclosed above, the biological entities may be introduced in the extruder in a powder or liquid form, such as a liquid formulation comprising a stabilizing and/or solubilizing component (e.g., water, glycerol, sorbitol, dextrin, including maltodextrine and cyclodextrine, starch, glycol such as propanediol, salt, etc.).

Particularly, such extruder may contain a principal hopper and several successive heating zones, wherein the temperature may be independently controlled and regulated and wherein additional components may be added at different time during the process.

Advantageously the anti-acid filler is introduced at a late stage of the mixing step and more particularly when the polyester is in a partially or totally molten state. Thus a homogenous mix is favored.

Advantageously, the biological entities are introduced at a late stage of the mixing step (i.e., in the last heating zones), and more particularly when the polyester is in a partially or totally molten state and after the anti-acid filler has been added. Thus, the exposure to elevated temperature is reduced. Preferably, the residence time of the biological entities in the extruder is half as long as the residence time of the polyester and/or anti-acid filler, or less.

According to the invention, after step (a) of mixing, the mixture may be conditioned (b) in any suitable solid form. In this regard, in a preferred embodiment, the mixture issued from step (a) is shaped into a rod through a die. The rod is then cooled, and optionally dried before to be chopped in the form of granulates of plastic composition. In a further embodiment, said granulates of plastic composition may be pulverized or micronized to produce a powder of said plastic composition.

When the mixture issued of step (a) is a powder mixture, it is possible to submit the powder mixture to an extrusion-granulation process, preferably in an extruder so that the mixture is in a partially or totally molten state, before step (b).

Alternatively, the mixture issued of step (a) may be agglomerated in a solid physical form.

In a particular embodiment, the present invention relates to a process for preparing a plastic composition, comprising a step (a) of mixing between 0.1% and 10% by weight of proteases having a PLA-degrading activity, based on the total weight of the plastic composition, with PLA and an anti-acid filler and a step (b) of conditioning said mixture of step (a) in a solid form, wherein the step (a) of mixing is preferably performed at a temperature between 150 and 180° C. and/or in an extruder, preferably a twin-screw extruder, and more preferably a co-rotative twin-screw extruder, and wherein the anti-acid filler is preferably selected from hydrotalcite, calcium carbonate and/or calcium hydroxide.

In another particular embodiment, the present invention relates to a process for preparing a plastic composition, comprising a step (a) of mixing between 0.1% and 10% by weight of lipases having a PCL-degrading activity, based on the total weight of the plastic composition, with PCL and an anti-acid filler and a step (b) of conditioning said mixture of step (a) in a solid form, wherein the step (a) of mixing is preferably performed at a temperature between 60 and 80° C. and/or in an extruder, preferably a twin-screw extruder, and more preferably a co-rotative twin-screw extruder, and wherein the anti-acid filler is preferably selected from hydrotalcite, calcium carbonate and/or calcium hydroxide.

In another particular embodiment, the plastic composition may be obtained via an enzyme adsorption process (Jesionowski et al., Adsorption (2014) 20:801-821). The person skilled in the art will easily adapt the process to the type of plastic composition, biological entities and/or anti-acid filler.

More generally, the plastic composition may be produced by any techniques known by a person skilled in the art.

Plastic Articles

The invention also relates to the use of such plastic compositions for manufacturing plastic articles with improved and/or controlled degradability.

It is also an object of the invention to provide a plastic article made with the plastic composition of the invention, wherein the biological entities of the plastic composition are suitable for degrading at least one polyester of the plastic article and the anti-acid filler is able to enhance the degrading activity of the biological entities.

Therefore, the invention relates to a method for manufacturing a plastic article comprising at least one polyester, the method comprising:

A. providing a plastic composition of the invention; and
B. shaping said plastic composition into a plastic article.

Advantageously, step B is implemented at a temperature at which the polyester of the plastic composition is in a partially or totally molten state. For instance, step B may be performed at a temperature at or above 40° C., particularly at or above 45° C., 55° C., 60° C., 70° C., 80° C., 90° C., 100° C., or even above 150° C., depending on the nature of the polyester in the plastic composition. Typically, this temperature does not exceed 300° C. More particularly, the temperature does not exceed 250° C. The temperature of the step B can be adapted by a person skilled in the art depending on the type of the plastic composition and/or the kind of plastic articles intended. Particularly, the temperature is chosen according to the melting point, or melting temperature of the polyester of the plastic composition.

In a particular embodiment, step B is performed at the melting point of the polyester. The polyester is then in a partially or totally molten state. In another embodiment, step B is performed at a temperature between the glass transition temperature (Tg) and the melting point of said polyester. In another particular embodiment, step B is performed at a temperature above the melting point of said polyester.

Typically, said step B may be carried out by extrusion, extrusion-compounding, extrusion blow-molding, blown film extrusion, cast film extrusion, calendering and thermoforming, injection-molding, compression molding, extrusion-swelling, rotary molding, ironing, coating, stratification, expansion, pultrusion, compression-granulation, or 3D printing. Such operations are well known by the person skilled in the art, who will easily adapt the process conditions (e.g., temperature, residence time, etc.).

In a particular embodiment, step B is implemented with a solid plastic composition under a powder or granulated form, preferably under a granulated form. In another embodiment, step B is implemented with a liquid plastic composition.

Advantageously, the resulting plastic article is a biodegradable plastic article complying with at least one of the relevant standards and/or labels known by a person skilled in the art such as standard EN 13432, standard ASTM D6400, OK Biodegradation Soil (Label Vincotte), OK Biodegradation Water (Label Vincotte), OK Compost (Label Vincotte), OK Compost Home (Label Vincotte).

A biodegradable plastic article refers to a plastic that is at least partially transformed under environmental conditions into oligomers and/or monomers of at least one polyester of the plastic article, water, carbon dioxide or methane and biomass. For instance, the plastic article is biodegradable in water. Preferably, about 90% by weight of the plastic article is biodegraded in water within less than 90 days, more preferably within less than 60 days, even more preferably within less than 30 days. More preferably, the plastic article may be biodegraded when exposed to wet and temperature conditions that occur in landscape. Preferably, about 90% by weight of the plastic article is biodegraded with less than 3 years in the environment, more preferably within less than 2 years, even more preferably within less than 1 year. Alternatively, the plastic article may be biodegraded under industrial composting conditions, wherein the temperature is maintained above 50° C.

The invention also provides a method for increasing the biodegradability of a plastic article comprising at least one polyester, wherein the method comprises the step of mixing a polyester with both biological entities suitable for degrading said polyester and anti-acid filler to obtain a plastic composition and the step of manufacturing a plastic article with said plastic composition.

EXAMPLES

Example 1—Plastic Composition Comprising Polylactic Acid (PLA), Savinase®, and Calcium Carbonate or Calcium Hydroxide as Anti-Acid Filler

1A—Process of Manufacturing the Plastic Composition Through an Extrusion Process The formulations A-E (table 3) were prepared in order to assess the ability of Calcium carbonate ($CaCO_3$) or Calcium hydroxide ($Ca(OH)_2$), as anti-acid fillers, to increase the degradation of PLA compositions.

TABLE 3

| | \multicolumn{5}{c}{Formulations} | | | | |
|---|---|---|---|---|---|
| | PLA | Protease (Savinase ®) | Dextrin | $CaCO_3$ | $Ca(OH)_2$ |
| A | 95% | 2.5% | 2.5% | — | — |
| B | 95% | 2.5% | — | 2.5% | — |
| C | 95% | 2.5% | — | — | 2.5% |
| D | 95% | — | 2.5% | 2.5% | — |
| E | 95% | — | 2.5% | — | 2.5% |

Percentages are given by weight, based on the total weight of the formulation.

A corresponds to the control: the anti-acid filler has been replaced by a neutral dextrin;

D and E correspond to negative controls, deprived of protease.

The formulations have been prepared using:

PLA (polylactic acid polymer, PLA 4043D from NatureWorks), under a powder form (<500 μm) obtained from PLA pellets immersed in liquid nitrogen and micronized using an Ultra Centrifugal Mill ZM 200 system.

Savinase® 16L from Novozymes, under solid form, that is known to have the ability to degrade PLA (Degradation of Polylactide by commercial proteases; Y. Oda, A. Yonetsu, T. Urakami and K. Tonomura; 2000). Solid Form of Savinase® 16L was obtained from commercial liquid form by ultrafiltration on 3.5 kDa membrane, diafiltration, addition of dextrin and drying by freeze-drying.

dextrin (MALDEX 190 Wheat from Terreos) or calcium carbonate ($CaCO_3$ from OMYA) or calcium hydroxide ($Ca(OH)_2$ from Sigma Aldrich).

Based on these formulations, biodegradable polylactic acid-based plastic compositions have been prepared through an extrusion process.

A compounding machine, or co-rotating twin-screw extruder, has been used ("Haake MiniLab II ThermoFisher"). This compounding machine comprised successively a manual feed element, two co rotating screws and the head of the twin screw.

All powders were mixed together by manual shaking before introduction in the compounding machine. The mix was then introduced in the feeding zone, and push into the screw extruder applying manual pressure. The mix went through co-rotating screws using a rotation speed of the twin-screw of 80 RPM. The temperature of the extrusion was fixed to 165° C. The mix of PLA, biological entities and anti-acid filler (or dextrin) then arrived in the screw head, comprising one hole of 0.4 mm in diameter, wherein the mix was pushed in order to form strip shapes. This extrudate was then cut with cutting pliers to obtain the plastic composition under granulated form.

1B—Tests of Biodegradability of the Plastic Compositions

The biodegradability of the plastic compositions obtained from example 1A has been assessed.

100 mg of each granulated sample (from A to E) were weighted and introduced in dialysis tubing. 3 mL of 0.1 M Tris-HCl buffer pH 9.5 were added in the dialysis tubing before closing it. The dialysis tubing was then introduced in a plastic bottle containing 50 mL of 0.1 M Tris-HCl buffer pH 9.5.

The depolymerization was started by incubating each sample at 45° C., 150 rpm in an Infors HT Multitron Pro incubation shaker. Aliquots of 1 mL of buffer were sampled regularly, filtered on 0.22 μm syringe filter, and analyzed by High Pressure Liquid Chromatography (HPLC) with an Aminex HPX-87H column to monitor the liberation of lactic acid (LA) and lactic acid dimer (DP2). Chromatography system used was an Ultimate 3000 UHPLC system (Thermo Fisher Scientific, Inc. Waltham, Mass., USA) including a pump module, an autosampler, a column oven thermostated at 50° C., and an UV detector at 220 nm. Eluent was 5 mM $H_2SO_4$. Injection was 20 μL of sample. LA was measured according to standard curves prepared from commercial LA.

Hydrolysis of plastic articles was calculated based on LA and DP2 released. Percentage of degradation was calculated by the molar ratio of LA plus the LA contained in DP2 at a given time versus the LA contained initially in the PLA in the plastic composition. Results of depolymerization, after 12 days of test, are shown in FIG. 1.

The results show that the addition of $CaCO_3$ or $Ca(OH)_2$ to the plastic composition allows to increase significantly the degradation of the PLA.

Example 2—Plastic Compositions Comprising PLA, Protease and a Mix of Anti-Acid Fillers

2A—Process of Manufacturing the Plastic Compositions Through an Extrusion Process The following formulations A-C (table 4) were prepared in order to assess the ability of Calcium carbonate ($CaCO_3$) alone or mixed with Calcium hydroxide ($Ca(OH)_2$) as anti-acid fillers, to increase the degradation of PLA compositions.

TABLE 4

| | \multicolumn{4}{c}{Formulations} | | | |
|---|---|---|---|---|
| | PLA | Protease | $CaCO_3$ | $Ca(OH)_2$ |
| A | 90% | 10% | — | — |
| B | 85% | 10% | — | 5% |
| C | 85% | 10% | 2.5% | 2.5% |

Percentages are given by weight, based on the total weight of formulations.

The formulations have been prepared using

PLA, calcium carbonate and calcium hydroxide in powder form as described in Example 1A, a Protease enzyme from *Actinomadura keratinilytica* strain under solid form. Solid form of protease from *Actinomadura keratinilytica* was obtained from fermentation process, followed by ultrafiltration on 3.5 kDa membrane, diafiltration, addition of dextrin and drying by atomization. Such protease is known for degrading PLA as described in patent WO 2016/062695.

Based on these formulations, biodegradable polylactic acid-based plastic compositions have been prepared through an extrusion process. The extrusion process was the same as the one described in Example 1A.

2B—Tests of Biodegradability of the Plastic Compositions

The biodegradability of the plastic compositions obtained from example 2A has been assessed.

The depolymerization test was performed using the same material and method as exposed in Example 1.

Figure 2:
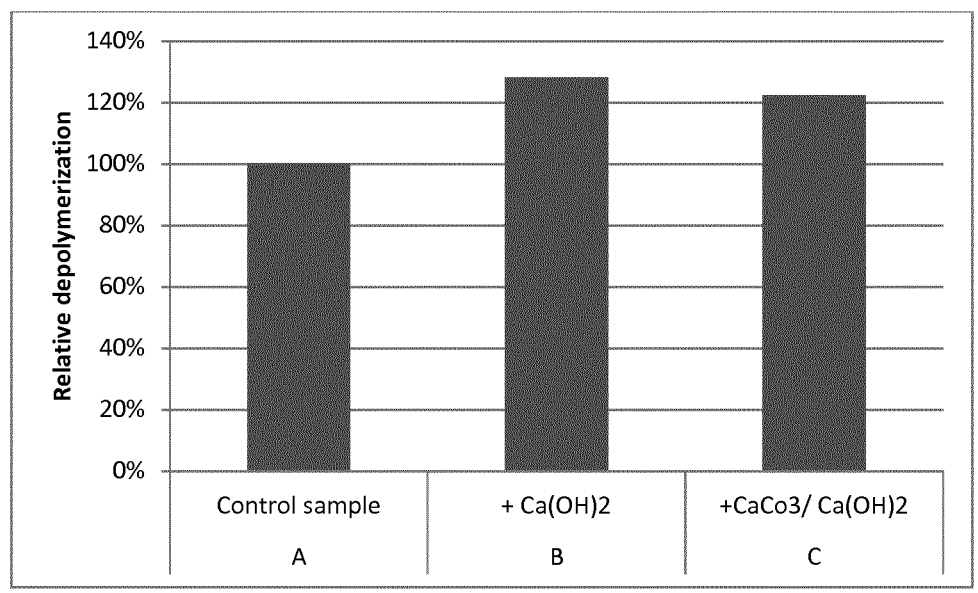
FIG. 2: Comparative depolymerization rate of plastic compositions containing PLA after 3 days. A: Control (comprising protease but deprived of anti-acid filler); B and C: plastic compositions according to the invention (comprising both protease and calcium hydroxide, or a mix of calcium carbonate and calcium hydroxide respectively). After 3 days, plastic compositions B and C show respectively 28% and 22% more depolymerization than the control A.

The hydrolysis of the plastic compositions was calculated based on LA and dimer of LA released. Percentage of degradation was calculated regarding the final percentage of PLA in the formulation. Results of depolymerization were expressed compared to the control sample A (without anti-acid filler, base 100%), after 3 days of test (FIG. 2).

The results show that the addition of both $CaCO_3$ and $Ca(OH)_2$ to the plastic composition also allows to enhance the degradation of PLA based composition.

Example 3—Plastic Compositions Comprising PLA, Protease and Natural or Commercial Mineral Acid Filler 3A—Process of Manufacturing Plastic Compositions Through an Extrusion Process The efficiency of both a mineral synthetic acid scavenger (DHT4-A2) and a mineral natural acid scavenger ($CaCO_3$) has been evaluated and compared.

The following formulations A-C (Table 5) were prepared in order to assess the ability of a commercial hydrotalcite (Magnesium Aluminium Hydroxide Carbonate (DHT4-A2)), to increase the degradation of PLA compositions.

TABLE 5

| | Formulations | | | |
|---|---|---|---|---|
| | PLA | Protease | CaCo3 | DHT4-A2 |
| A | 95% | 5% | — | — |
| B | 90% | 5% | 5% | — |
| C | 90% | 5% | — | 5% |

Percentages are given by weight, based on the total weight of formulations.

The formulations have been prepared using PLA and calcium carbonate in powder form as described in Example 1A, a Protease enzyme from *Actinomadura keratinilytica* strain under solid form as described in Example 2A, and DHT4-A2 (from Kyowa Chemical Industry).

Based on these formulations, biodegradable polylactic acid-based plastic compositions have been prepared through an extrusion process as the one described in Example 1.A 3B—Tests of Biodegradability of the Plastics Compositions The biodegradability of the plastic compositions obtained from example 3A has been assessed.

The depolymerization test was performed using the same material and method as exposed in Example 1.

Figure 3:
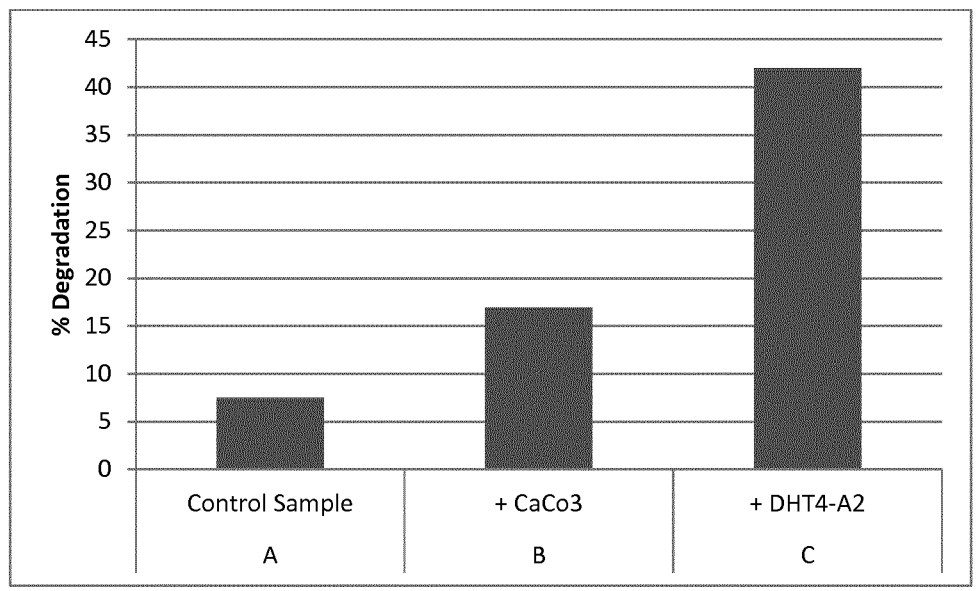
FIG. 3: Comparative degradation rate of plastic compositions containing PLA after 2 days. A: Control (comprising protease but deprived of anti-acid filler) reached 7.5% degradation. B and C: plastic compositions according to the invention (comprising both protease and calcium carbonate and hydrotalcite respectively as anti-acid filler) reached about 17% and 42% biodegradation respectively.

The hydrolysis of the plastic compositions was calculated based on LA and dimer of LA released. Percentage of degradation was calculated regarding the final percentage of PLA in the formulation. Results of depolymerization, after 2 days of test, are shown in FIG. 3.

The results show that, after two days of tests, the degradation rate of the composition C, comprising the commercial hydrotalcite is more than twice higher than the degradation rate of the composition comprising the natural calcium carbonate.

Example 4—Plastic Composition Comprising PLA, Savinase®, and Various Amounts of Calcium Carbonate ($CaCO_3$)

4A—Process of Manufacturing Plastic Compositions Through an Extrusion Process

The efficiency of Calcium carbonate ($CaCO_3$) at a higher concentration has been evaluated.

To this end, different formulations A-C (table 6) have been prepared.

TABLE 6

| | Formulations | | | |
|---|---|---|---|---|
| | PLA | Protease | Dextrin | $CaCo_3$ |
| A | 95% | 5% | — | — |
| B | 70% | — | — | 25% |
| C | 70% | 5% | — | 25% |

Percentages are given by weight, based on the total weight of formulations.

A corresponds to a control sample (without anti-acid filler) and B corresponds to a negative control (without protease).

The formulations comprising PLA, Protease Savinase® 16L, and calcium carbonate in powder form have been prepared as described in Example 1A.

Based on these formulations, biodegradable polylactic acid-based plastic compositions have been prepared through an extrusion process as described in Example 1.A 4B—Tests of Biodegradability of the Plastic Compositions The biodegradability of the plastic compositions obtained from example 4A has been assessed.

The depolymerization test was performed using the same material and method as exposed in Example 1.

Figure 4:
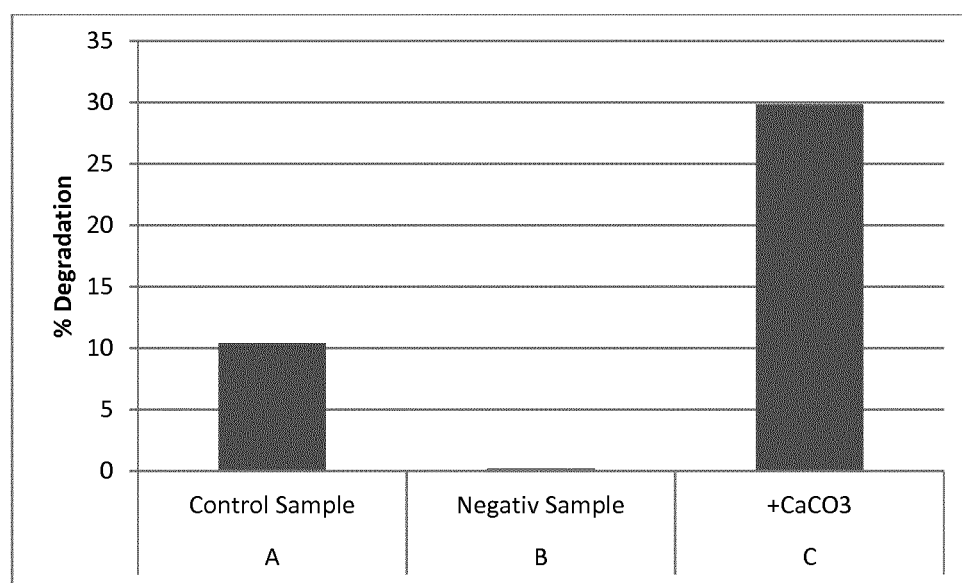
FIG. 4: Comparative degradation rate of plastic compositions containing PLA after 3 days. A: Control (comprising protease but deprived of anti-acid filler) reached 10% of degradation; B: Negative controls (comprising anti-acid filler but deprived of protease) reached less than 1% of degradation; and C: plastic composition according to the invention (comprising protease and 25% of an anti-acid filler) reached 30% of degradation.

Hydrolysis of plastic articles was calculated based on LA and dimer of LA released. Percentage of degradation was calculated regarding the final percentage of PLA in the formulation. Results of depolymerization, after 3 days of test, are shown in FIG. 4.

Example 5—Plastic Compositions Comprising PLA, Everlase®, and Calcium Carbonate

5A—Process of Manufacturing Plastic Compositions Through an Extrusion Process

According to this experiment, the ability of calcium carbonate to enhance the degradation activity of Everlase® contained in a PLA composition has been assessed.

To this end, the formulations A and B have been prepared:
Formulation A=95% of PLA+5% of Everlase®
Formulation B=90% of PLA+5% of Everlase®+5% of calcium carbonate Percentage was calculated by weight based on the total weight of composition.

Compositions have been prepared comprising PLA in solid form (polylactic acid polymer, PLA XP951/B by Accurel) and calcium carbonate as described in Example 1 and Everlase® 16L from Novozymes, under solid form (reformulated in the solid state with dextrin). Solid Form of Everlase® 16L was obtained from commercial liquid form by diafiltration, addition of dextrin and drying by freeze-drying.

Based on these formulations, biodegradable polylactic acid-based plastic compositions have been prepared through an extrusion process.

Extrusion process used was the same as the one described in Example 1A.

5B—Tests of Biodegradability of Plastic Compositions

The biodegradability of said plastic compositions has been further tested.

100 mg of sample A and B were each introduced in a plastic bottle containing 50 mL of 0.1 M Tris-HCl buffer pH 9.5. The depolymerization was started by incubating each sample at 45° C., 150 rpm in a Infors HT Multitron Pro incubation shaker. Aliquots of 1 mL of buffer were sampled regularly and filtered on 0.22 µm syringe filter. Samples were analyzed following the same material and method described in example 1A.

Figure 5:
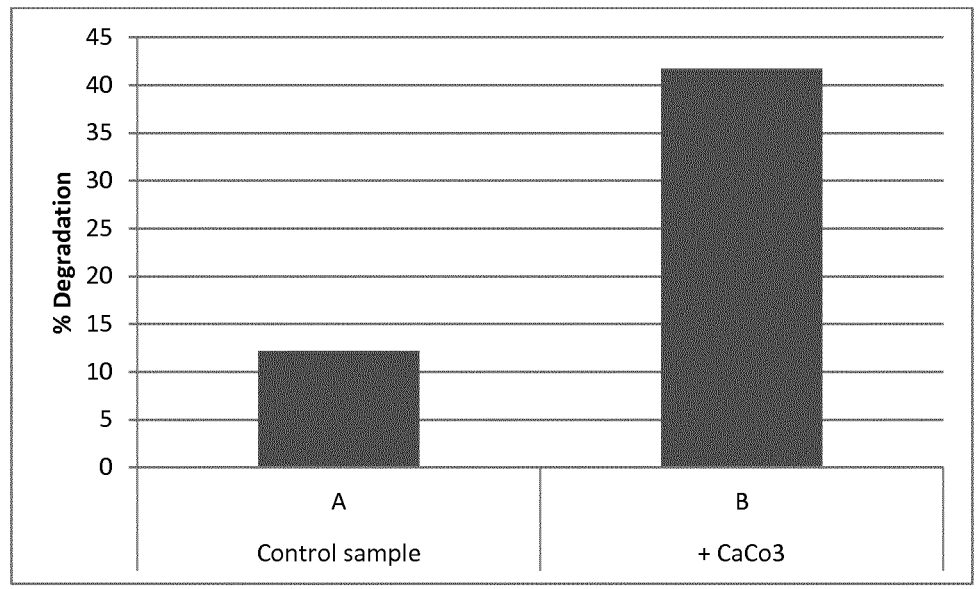
FIG. 5: Comparative degradation rate of two plastic compositions containing PLA after 3 days. B: Plastic composition according to the invention (comprising both protease and calcium carbonate) reached 42% of degradation after 3 days whereas A: Control (comprising protease but deprived of calcium carbonate) reached solely 12% of degradation.

Hydrolysis of plastic articles was calculated based on LA and dimer of LA released. Percentage of degradation is calculated regarding the final percentage of PLA in the formulation. Results of depolymerization, after 3 days of test, are shown in FIG. 5.

Example 6—Plastic Compositions Comprising Polycaprolactone (PCL), Lipase and Calcium Carbonate ($CaCO_3$)

6A—Process of Manufacturing Plastic Compositions Through an Extrusion Process

Two formulations A and B (Table 7) were prepared to evaluate the influence of calcium carbonate on plastic composition containing PCL:

TABLE 7

| | Formulations | | |
|---|---|---|---|
| | PCL | Lipase | CaCo3 |
| A | 95% | 5% | — |
| B | 90% | 5% | 5% |

Percentage was calculated by weight based on the total weight of composition.

The formulations have been prepared using:

PCL in powder form (polycaprolactone polymer, CAPA 6500 from Perstorp). PCL is used under a powder form (<1 mm) obtained from PCL granulate immersed in liquid nitrogen and micronized using an Ultra Centrifugal Mill ZM 200 system.

a lipase enzyme under solid form (Amano Lipase PS from Amano), known for degrading PCL and calcium carbonate (from OMYA).

Based on these formulations, biodegradable PCL-based plastic compositions have been prepared through an extrusion process.

All powders were mixed together by manual shaking before introduction in the compounding machine (same compounding machine used as in example 1A). The mix was then introduced in the feeding zone, and pushed into the screw extruder applying manual pressure. The mix went through co-rotating screw, through the rotation of the twin-screw at 80 RPM. The temperature was fixed to 80° C. The mix of polymer, biological entities and anti-acid filler then arrived in the screw head, comprising one hole of 0.4 mm long, wherein the mix was pushed in order to form strip shapes. This extrudate was then cut with cutting pliers to obtain granulate form.

6B—Tests of Biodegradability of Plastics Compositions

The biodegradability of said plastic compositions has been further assessed.

To this end, 500 mg of each sample were weighted and introduced in a plastic bottle containing 25 mL of osmosis water.

The depolymerization was started by incubating each sample at 45° C., 150 rpm in a Infors HT Multitron Pro incubation shaker. Aliquots of 1 mL of buffer were sampled regularly and filtered on 0.22 µm syringe filter, samples were analyzed by High Pressure Liquid Chromatography (HPLC) with an Aminex HPX-87H column to monitor the liberation of 6-hexanoic acid (HHA). Chromatography system used was an Ultimate 3000 UHPLC system (Thermo Fisher Scientific, Inc. Waltham, Mass., USA) including a pump module, an autosampler, a column oven thermostated at 50° C., and an UV detector at 220 nm. Eluent was 5 mM $H_2SO_4$. Injection was 20 µL of sample. HHA was measured according to standard curves prepared from commercial HHA (Alfa Aesar).

Figure 6:
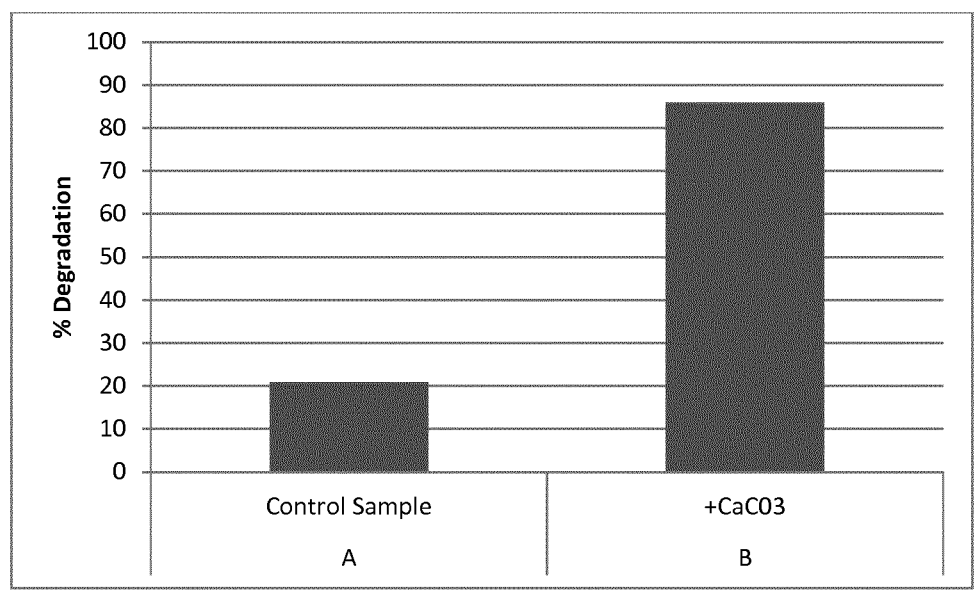
FIG. 6: Comparative degradation rate of two plastic compositions comprising PCL and lipase after 3 days. B (with calcium carbonate) reached 86% of degradation, whereas Control A (without calcium carbonate) reached 21% of degradation.

Hydrolysis of plastic articles was calculated based on HHA released. Percentage of degradation is calculated regarding the final percentage of PCL in the formulation. Results of depolymerization, after 3 days of test, are shown in FIG. 6.

The results show that the addition of $CaCO_3$ to the plastic composition allows to increase significantly the degradation of the PCL.

The invention claimed is:

1. A method for increasing polyester degrading activity of biological entities in a plastic composition consisting of at least one polyester selected from the group consisting of polylactic acid (PLA), polycaprolactone (PCL), polybutylene adipate terephthalate (PBAT), polyhydroxyalkanoate (PHAs) and polybutylene succinate (PBS), at least one anti-acid filler, and biological entities, said method comprising the steps of:
    (a) selecting the at least one polyester;
    (b) selecting biological entities, said biological entities comprising an enzyme suitable for degrading the at least one polyester of step (a) and/or a microorganism expressing an enzyme suitable for degrading the polyester of step (a);
    (c) selecting at least one mineral anti-acid filler;
    (d) mixing said at least one polyester with said biological entities and said at least one mineral anti-acid in order to increase the degrading activity of said enzyme and to obtain said plastic composition; and
    (e) manufacturing a plastic article with said plastic composition,
    and wherein the plastic composition comprises between 2% and 25% by weight of said at least one mineral anti-acid filler.

2. The method of claim 1, wherein the at least one mineral anti-acid filler is selected from carbonate salts, metals, hydroxide salts, hydrotalcite, talc, mica, and clay.

3. The method of claim 1, wherein the at least one polyester of step (a) is selected from polylactic acid (PLA) or polycaprolactone (PCL).

4. The method of claim 1, wherein the biological entities are selected from a depolymerase, esterase, lipase, cutinase, carboxylesterase, protease, and polyesterase.

5. The method of claim 1, wherein mixing in step (d) is implemented at a temperature at which the polyester of said plastic composition is in a partially or totally molten state.

6. The method of claim 1, wherein mixing in step (d) is performed by a method selected from extrusion, extrusion-compounding, extrusion blow-molding, blown film extrusion, cast film extrusion, calendering and thermoforming, injection-molding, compression molding, extrusion-swelling, rotary molding, ironing, coating, stratification, expansion, pultrusion, compression-granulation and 3D printing.

7. The method of claim 1, wherein mixing in step (d) is performed in an extruder selected from a twin-screw extruder, and a co-rotative twin-screw extruder.

8. The method of claim 4, wherein the biological entities are a lipase or protease.

9. The method of claim 1, wherein the plastic composition comprises between 2% and 15% by weight of the mineral anti-acid filler.

* * * * *